(12) United States Patent
Ruane (10) Patent No.: US 7,141,015 B2
(45) Date of Patent: Nov. 28, 2006

(54) EXPANDABLE AND PIVOTALLY ADJUSTABLE SURGICAL RETRACTOR

(76) Inventor: Bernard Joseph Ruane, 17 Ashe Street, Tralee, Co Kerry (IE)

( * ) Notice: Subject to any disclaimer, the term of this patent is extended or adjusted under 35 U.S.C. 154(b) by 189 days.

(21) Appl. No.: 10/434,559

(22) Filed: May 9, 2003

(65) Prior Publication Data

US 2004/0225196 A1    Nov. 11, 2004

(51) Int. Cl.
*A61B 1/00*    (2006.01)
*A61B 1/04*    (2006.01)
(52) U.S. Cl. ........................... 600/220; 600/219
(58) Field of Classification Search ............... 600/220, 600/221, 222, 215, 223, 224, 225, 213, 214, 600/210, 201, 219; 606/119
See application file for complete search history.

(56) References Cited

U.S. PATENT DOCUMENTS

| 3,176,682 | A | * | 4/1965 | Wexler ...................... 600/219 |
| 3,851,642 | A |   | 12/1974 | McDonald |
| 3,985,125 | A |   | 10/1976 | Rose |
| 4,263,899 | A | * | 4/1981 | Burgin ........................ 600/213 |
| 4,763,669 | A |   | 8/1988 | Jaeger |
| 5,529,571 | A | * | 6/1996 | Daniel ........................ 600/219 |
| 5,785,648 | A | * | 7/1998 | Min ............................ 600/206 |
| 5,916,151 | A |   | 6/1999 | Charters |
| 5,931,777 | A | * | 8/1999 | Sava ........................... 600/213 |
| 5,984,867 | A | * | 11/1999 | Deckman et al. ........... 600/232 |
| 6,196,969 | B1 | * | 3/2001 | Bester et al. ................ 600/224 |
| 6,280,379 | B1 |   | 8/2001 | Resnick |
| 6,302,842 | B1 |   | 10/2001 | Auerbach et al. |
| 6,379,299 | B1 |   | 4/2002 | Borodulin et al. |
| 6,663,562 | B1 | * | 12/2003 | Chang ........................ 600/219 |
| 6,964,675 | B1 | * | 11/2005 | Zhu et al. ................... 606/213 |
| 2002/0022771 | A1 |   | 2/2002 | Diokno et al. |
| 2003/0055319 | A1 |   | 3/2003 | Chang |

FOREIGN PATENT DOCUMENTS

| GB | 1408382 | 10/1975 |
| WO | WO 2004/002323 | 1/2004 |

* cited by examiner

*Primary Examiner*—Pedro Philogene
(74) *Attorney, Agent, or Firm*—Oyen Wiggs Green & Mutala LLP (57) ABSTRACT

A surgical retractor is disclosed comprising first and second arms, each arm having a utility end and a handle end; first and second blades connected to the utility end of the first and second arms, each blade being pivotally adjustable about the longitudinal axis of the utility end of the associated arm; the first and second arms are adjustably connected between a closed position and an open position. The surgical retractor has particular application as a vaginal speculum.

17 Claims, 13 Drawing Sheets

EXPANDABLE AND PIVOTALLY ADJUSTABLE SURGICAL RETRACTOR

FIELD OF THE INVENTION

This invention relates to medical surgical instruments, particularly surgical retractors. This invention has application as a hand held or manipulated speculum for gynaecological examinations and operations.

BACKGROUND

Tears along the vaginal wall can be a common problem during childbirth, particularly when an expectant mother pushes the baby towards the birth canal prior to full dilation of the mother's cervix. This involves tearing the tissue of the cervix and the vagina wall. When this occurs, the mother may require post-birth surgery to stitch up the torn tissue, often under general anesthetic.

Tears of the vagina walls, the perinium (which is the area of tissue between the vagina and the anus), and the anus commonly occur during vaginal delivery. Natural perineal tears are referred to by their severity. First-degree tears involve tearing only the skin. Second-degree tears involve tearing muscle. Third-degree tears involve tearing the external anal sphincter muscle. Fourth-degree tears further involve tearing the rectal mucosa.

Sometimes the perinium is purposely cut by a doctor performing an episiotomy, which is an incision into the perinium to enlarge the size of the vaginal opening. A episiotomy is similar to a first or second-degree natural tear.

All of the above tearing or incisions usually require post-delivery operations to stitch up the area. Stitching fourth-degree tears is particularly difficult using known specula given that fourth-degree tears typically extend from the vagina wall all the way to the rectum.

A variety of surgical retractors are known for use during gynaecological examinations and are commonly called specula for this purpose. Specula generally have blades that are moveable between a closed position where the blades are in close proximity to each other and at least one open position wherein the blades are displaced with respect to each other to create an enlarged area within the vaginal canal near the cervix. The base end of each blade is typically connected to the body of the speculum around an enclosed opening of a limited size. A speculum can be adjusted so that the distance between the blades is expanded, allowing a physician to view and work with an expanded vaginal canal.

Existing specula can aid a physician in conducting inspections of the vagina and cervix. However, known speculum have shortcomings when used for surgery, particularly for surgery involving tears along the vaginal wall or cervix.

To stitch up tears of the cervix and vagina wall, it is common for doctors to use a speculum with blades that open to expand the vaginal cavity. This creates a larger opening near the cervix and a smaller opening near the entrance to the vagina.

The only access to a dilated vagina through a typical speculum is through an opening in the speculum that is bordered on all sides by parts of the speculum. This is an opening of limited size. For this reason, it is often difficult for a surgeon to have enough room to stitch a patient's cervix and vagina wall. A typical speculum encumbers or prevents a surgeon from stitching up the entrance of the vagina without removing the speculum.

An example of an existing speculum that encumbers the entrance of the vagina is disclosed in U.S. Pat. No. 3,985,125 issued to Rose. The Rose speculum has two limb members that are moveable with respect to each other. At the rear end of the main limb member is a yoke having two side walls and a free end portion. The only access to the dilated vagina using the Rose speculum is through an opening that is bordered by the main limb member, the side walls of the yoke, and the lower limb member.

U.S. patent application publication No. 2002/0022771 filed by Diokno et al. discloses a vaginal speculum with removable blades. Diokno discloses an upper blade that is pivotally adjustable with respect to the position of the remaining speculum to allow for a larger opening inside the vaginal cavity than at the entrance. When the Diokno blades are not removed, the entrance opening is of a fixed size. When at least one blade is removed, a remaining lower part can be used as a spatula.

Another known speculum uses scissor-type arms. U.S. Pat. No. 5,785,648 to Min discloses a speculum with manually operated scissor arms that have replaceable blade members. The speculum blades include a self-contained fiber optic light source. The Min invention does not disclose the ability to pivotally adjust the angle of the blades.

There exists a need for a surgical retractor suitable for operations wherein the displacement between two blades is both laterally expandable and pivotally adjustable. There is further a need for a surgical retractor that does not significantly encumber the vagina entrance when the retractor is in position for gynaecological operations.

SUMMARY OF THE INVENTION

A surgical retractor is disclosed having a first arm with a utility end and a handle end, a first blade connected to the utility end of the first arm, the first blade being pivotally adjustable about the longitudinal axis of the utility end of the first arm. The retractor has a second arm having a handle end and a utility end. A second blade is connected to the utility end of the second arm, the second blade being pivotally adjustable about the longitudinal axis of the utility end of the second arm. Attachment means connects the first and second arms and is adjustable between a closed position having a small distance between the utility end of the first arm and the utility end of the second arm and at least one open position having a larger distance between the utility end of the first arm and the utility end of the second arm.

The distance between the blades of the surgical retractor is both laterally expandable and pivotally adjustable. The surgical retractor does not significantly encumber the vagina entrance when the retractor is in position for gynaecological operations.

BRIEF DESCRIPTION OF DRAWINGS

In Figures which illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

FIGS. 1–5 show a preferred embodiment of the invention. This embodiment has a left arm (11) having a utility end and a handle end, the utility end attached to a left blade (13) and the handle end forming or attached to a left finger hole (34). The utility end of a right arm (12) is attached to a right blade (14) and the handle end of the right arm (12) forms or is attached to a right finger hole (35). The left and right arms (11, 12) are attached at a pivot connection (150). As seen in the figures, blades 13 and 14 are attached to arms 11 and 12 at or near a proximal end, and extend away from arms 11 and 12.

In the preferred embodiment shown in FIGS. 1–5, the distance between the utility ends of the left and right arms (11,12) is adjustable by increasing or decreasing the distance between the left and right finger holes (34, 35). The left and right arms (11,12) may be reversibly locked in position by a locking means such as finger lever (37) pressing against a ratchet lock (36). The finger lever (37) is normally urged to engage the ratchet lock (36) by a finger lever reinforcement (38). To increase the distance between the left and right finger holes (34, 35), thereby decreasing the distance between the blades (13, 14), the finger lever (37) is pulled towards the right finger hole (35). Pulling the finger lever (37) flexes the finger lever reinforcement (38) which is attached by a reinforcement screw (39).

In the preferred embodiment shown in FIGS. 1–5, the angular positions of the blades (13, 14) are adjustable by use of the rotation means described in this paragraph. In this embodiment, left and right blade shaft extensions (15, 16) are attached to the blade shafts (40) connecting the blades to the utility ends of the left and right arms (13, 14). Left and right fulcrums (19, 20) are integrally attached to the utility ends of the arms (13, 14). Left and right wires (23, 24) respectively extend from the ends of the left and right blade shaft extensions (15, 16), through an opening in the left and right fulcrums (19, 20), through a fulcrum sleeve (25) located near or at the pivot connection (150), and through a curved track (33) on a rotation disc (26) and into an adjustment arm (29). Left and right clips (21, 22) hold the end loops of each wire (23, 24) together at the ends of the left and right blade shaft extensions (15, 16). A third clip (not shown) holds the wires together and in position at the distal end (51) of fine adjustment screw (32). The rotation is effected in one of two ways: either by rotating the top rotation disc (26A) about a rotation axis or by adjusting the fine adjustment screw (32). These two manners of rotating the blades are described in detail with reference to FIG. 7 below.

Figure 1:
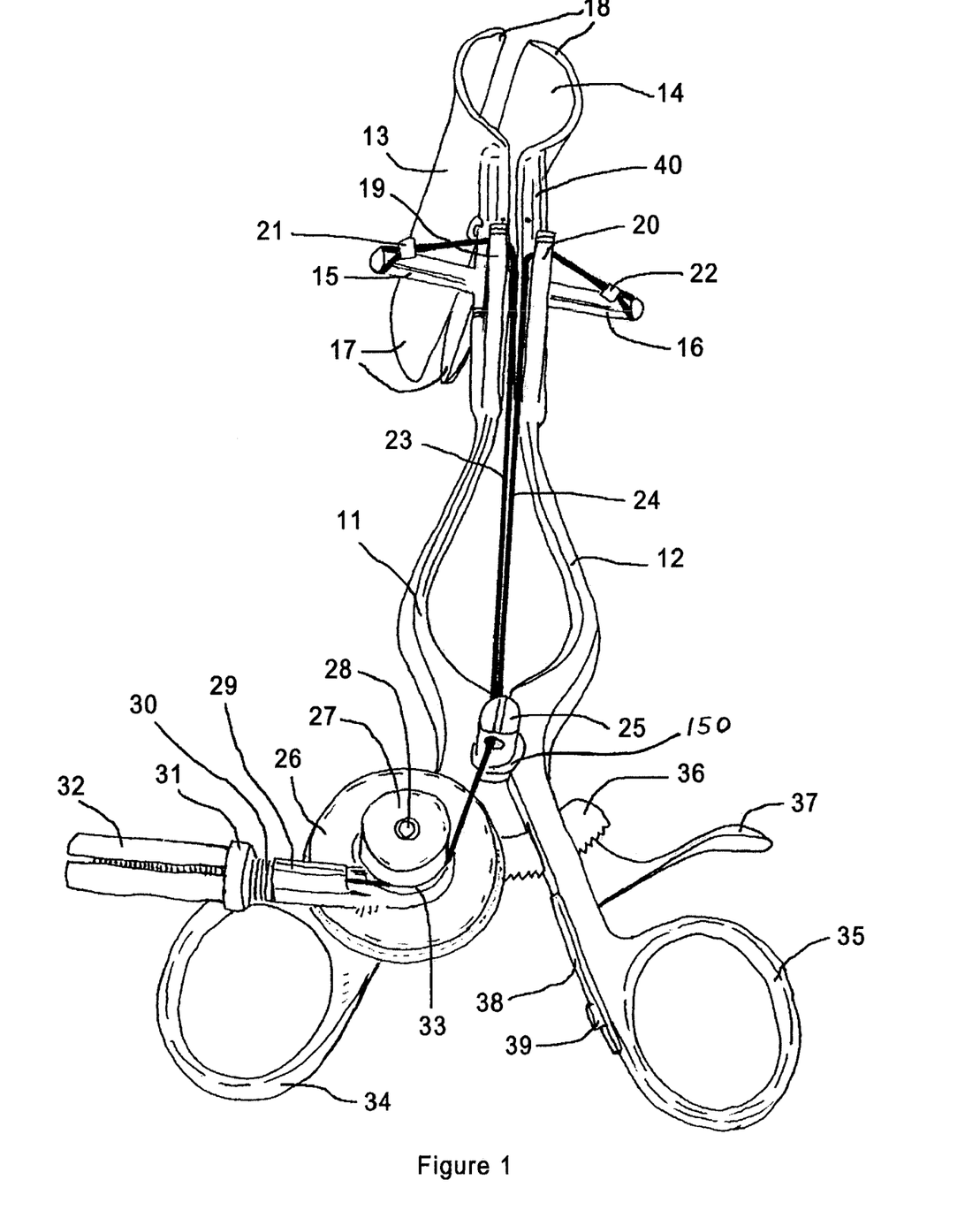
FIG. 1 is a top view of a preferred embodiment having blades in parallel position and in close proximity.
Figure 2:
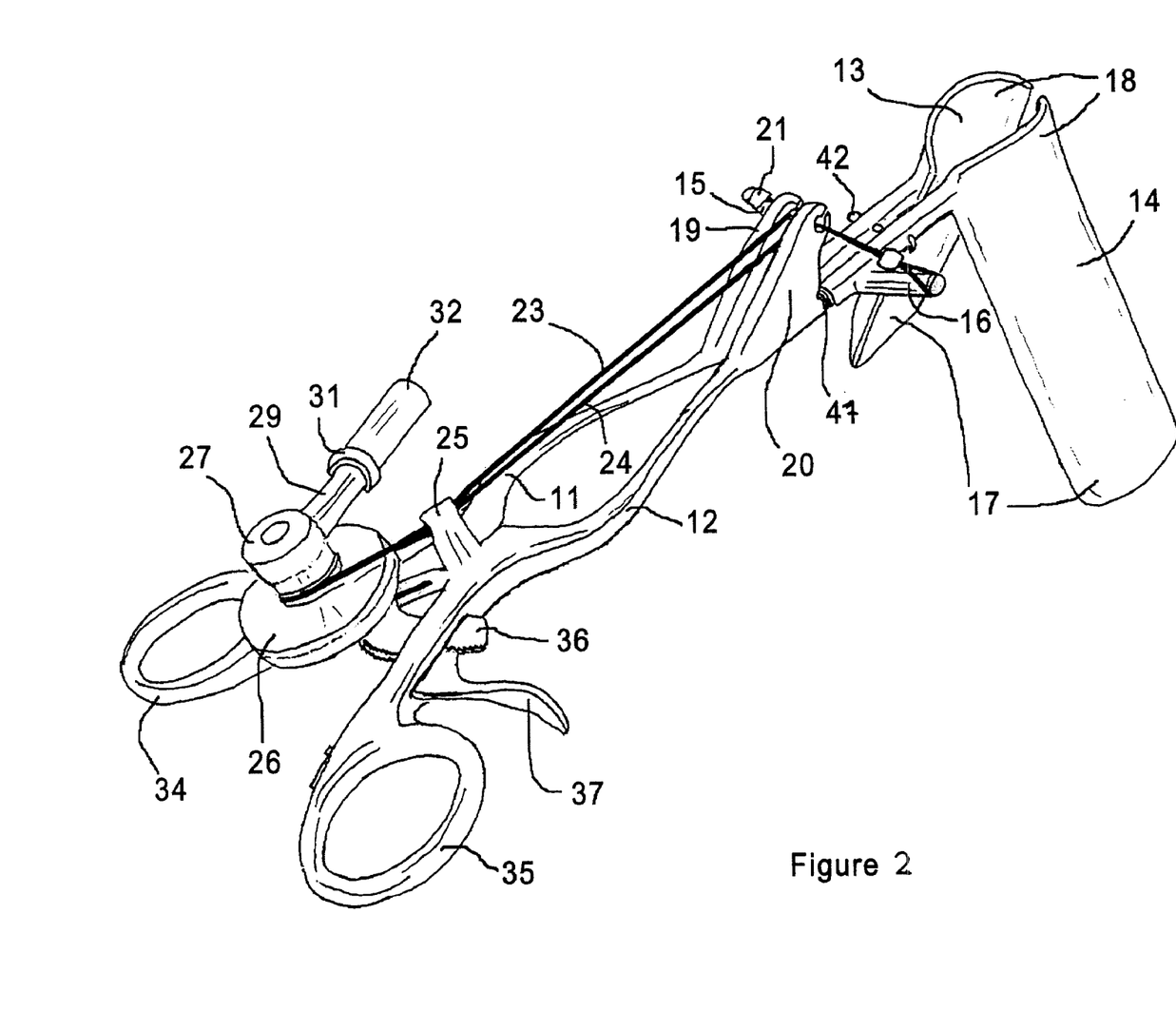
FIG. 2 is a side view of a preferred embodiment having blades in an angled position and in close proximity.

In FIG. 1, the left and right blades (13, 14) are shown in a closed position with the blades being in substantially parallel position and in close proximity to one another. In comparison with FIG. 1, each blade (13, 14) in FIG. 2 has been rotated about an axis co-linear with the axis of the utility end of the respective arm. In FIG. 2, the left and right blades (13, 14) are shown in close proximity and "splayed" or angularly displaced, such that there is a smaller distance between the proximal ends (18) than there is between the distal ends (17) of the blades (13, 14).

Figure 3:
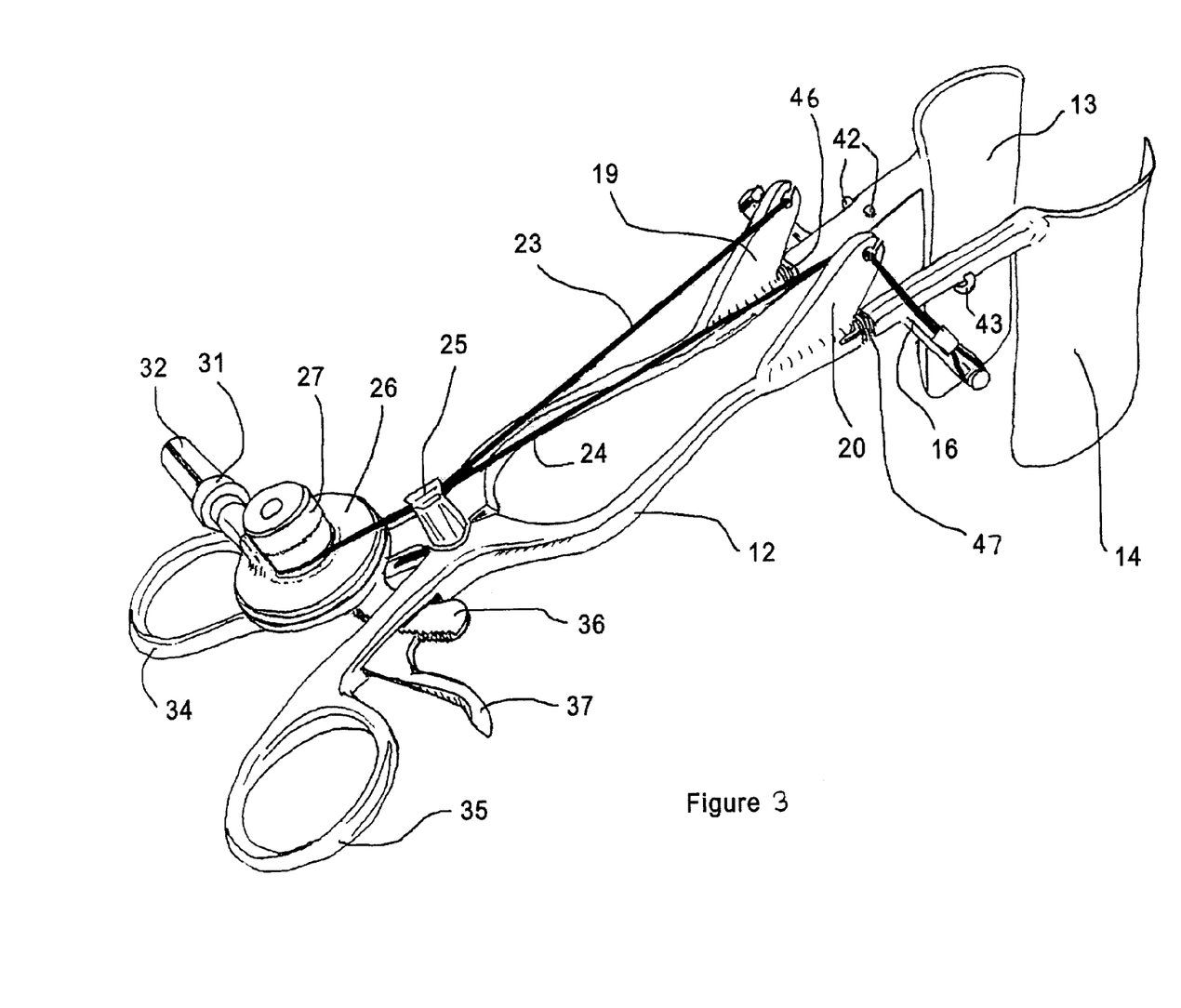
FIG. 3 is a side view of a preferred embodiment having blades in parallel position and laterally displaced.

As compared to FIG. 1, each blade in FIG. 3 remains in a parallel position but the displacement between the blades has been increased. In FIG. 3 the blades (13, 14) are shown in parallel position but laterally distanced from one another (i.e. not in close proximity).

Figure 4:
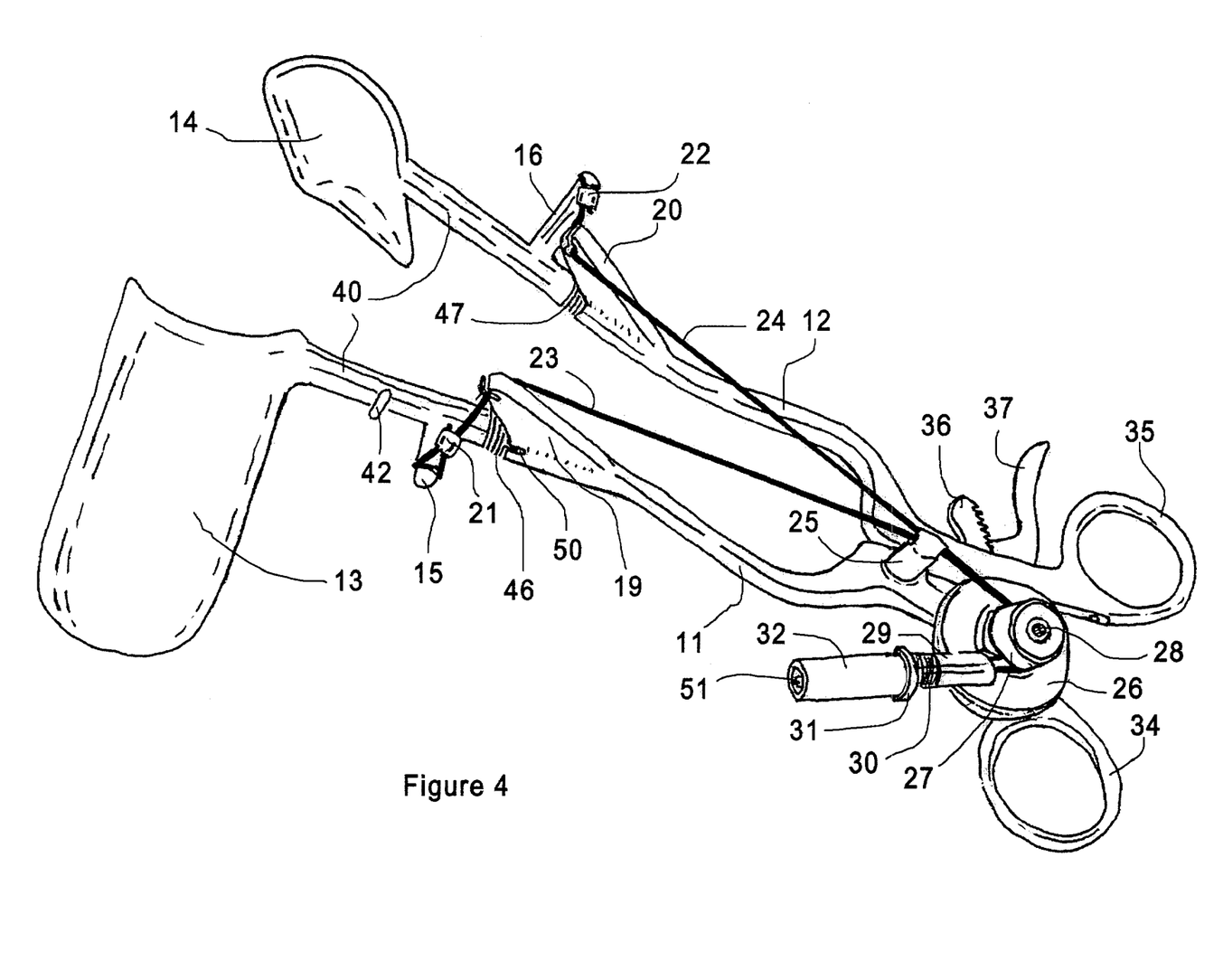
FIG. 4 is a side view of a preferred embodiment having blades in an angled position and laterally displaced.
Figure 5:
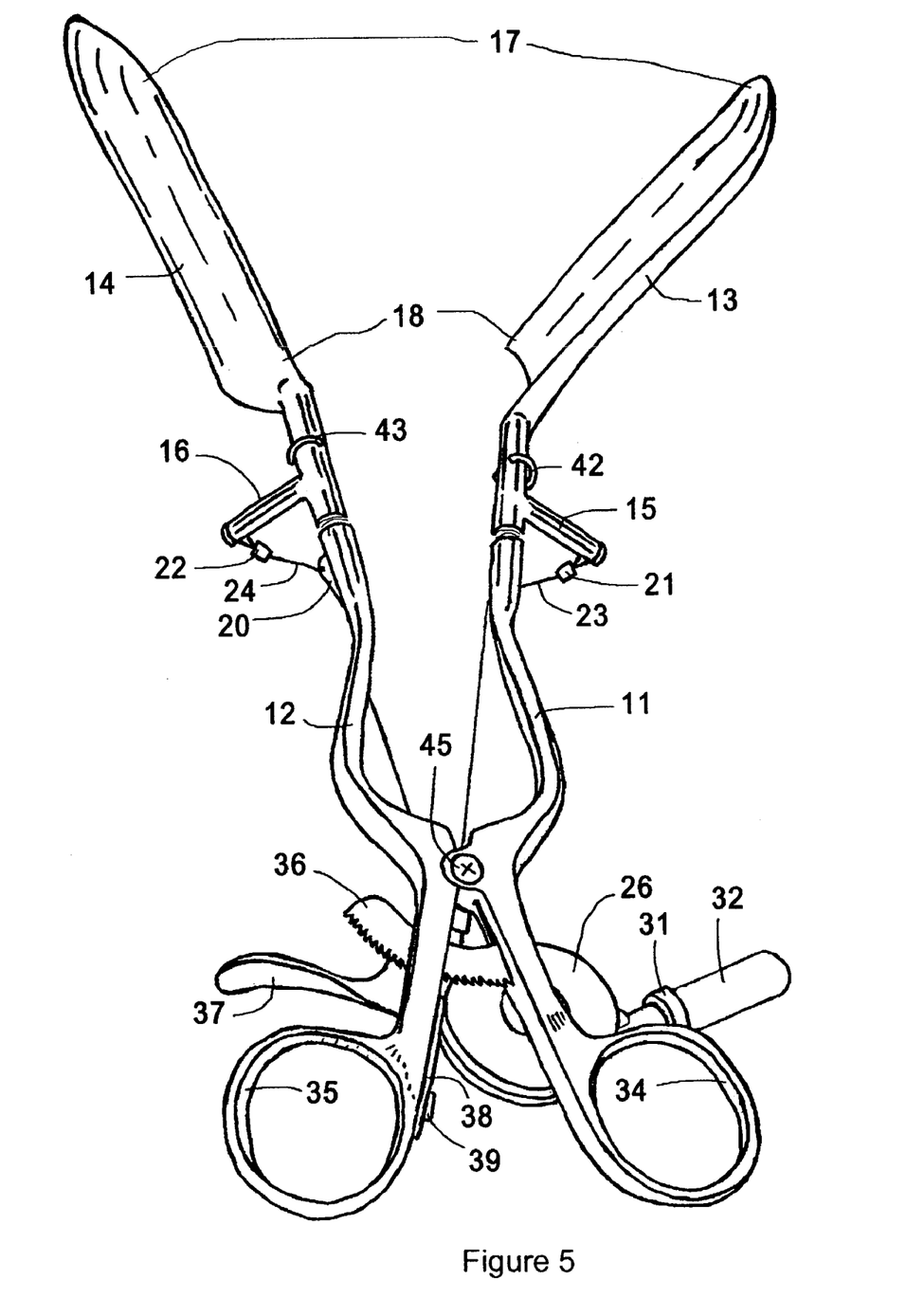
FIG. 5 is a bottom view of a preferred embodiment having blades in an angled position and laterally displaced.

As compared to FIG. 3, each blade in FIG. 4 has been rotated about an axis co-linear with the utility end of the respective arm. FIG. 5 shows a bottom view of the position of the preferred embodiment shown in FIG. 4. In both FIGS. 4 and 5, the left and right blades (13, 14) are shown to be angularly displaced and not in close proximity.

Figure 6A:
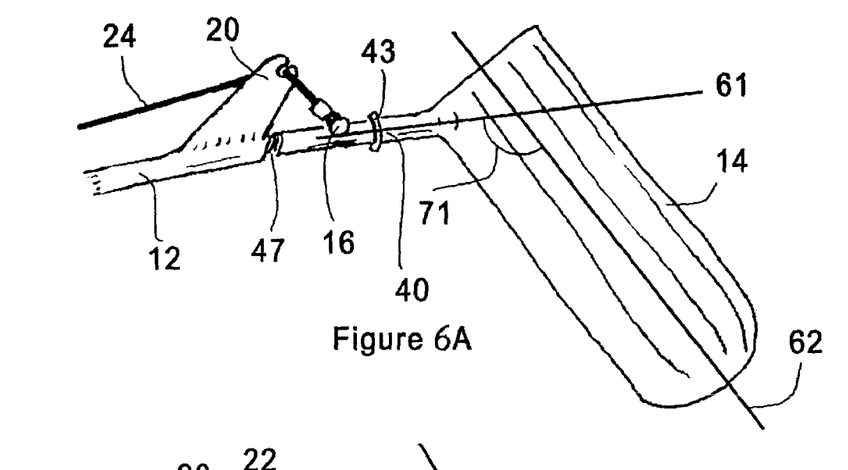
FIGS. 6A, 6B and 6C are partial side views of embodiments having blades connected to the arms at different angles.
Figure 6B:
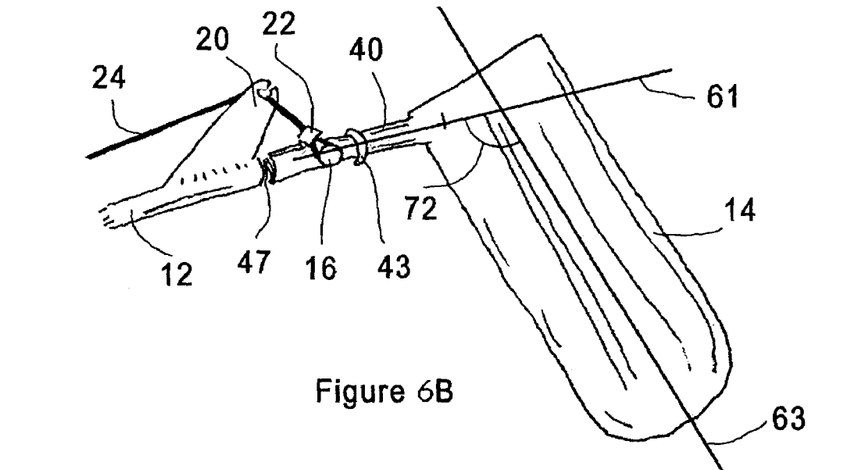
Figure 6C:
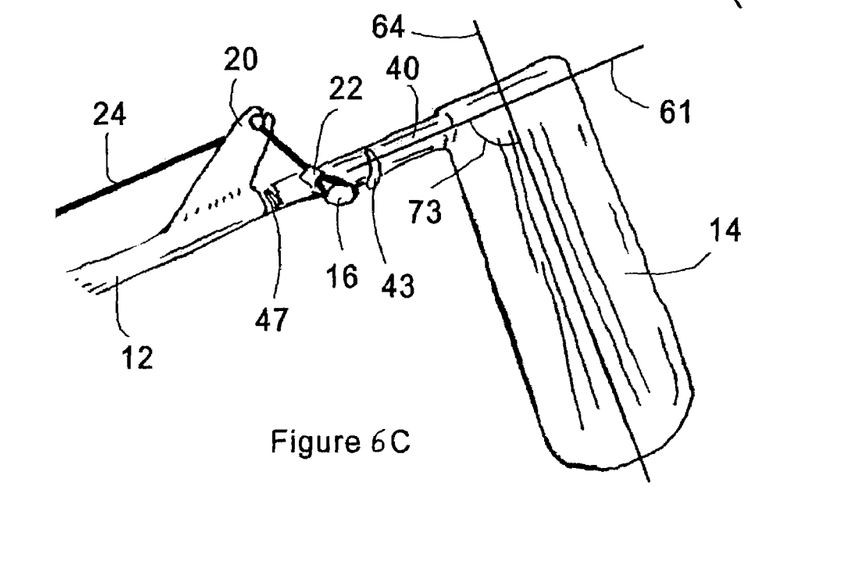

FIGS. 6A, 6B and 6C show side views of alternate embodiments for the angle of attachment between the longitudinal axis (61) of the utility end of the right arm (12) and the longitudinal axis of the right blade (14). FIG. 6A shows an embodiment where the angle (71) is approximately 120° between the longitudinal axis (61) of the utility end of the arm and the longitudinal axis (62) of the right blade (14). FIG. 6B shows an embodiment where the angle (72) is approximately 105°. FIG. 6C shows an embodiment where the angle (73) is approximately 90°. In each of these embodiments, the longitudinal axis (not shown in this perspective) of the left blade (13) is substantially parallel to the longitudinal axis (61) of the right blade (14). A physician can choose an embodiment having an angle that is most comfortable for positioning the invention. An alternate embodiment contains rotation means allowing rotation of the blade from the 90° angle shown in FIG. 6C through the 120° angle shown in FIG. 6A.

Figure 7:
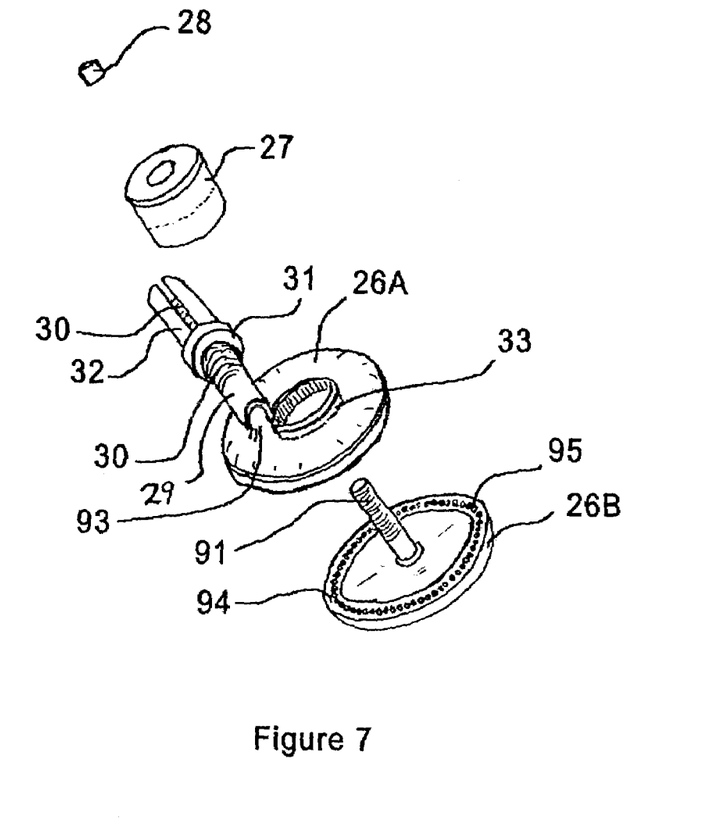
FIG. 7 is an exploded view of a preferred embodiment of rotation means.
Figure 8A:
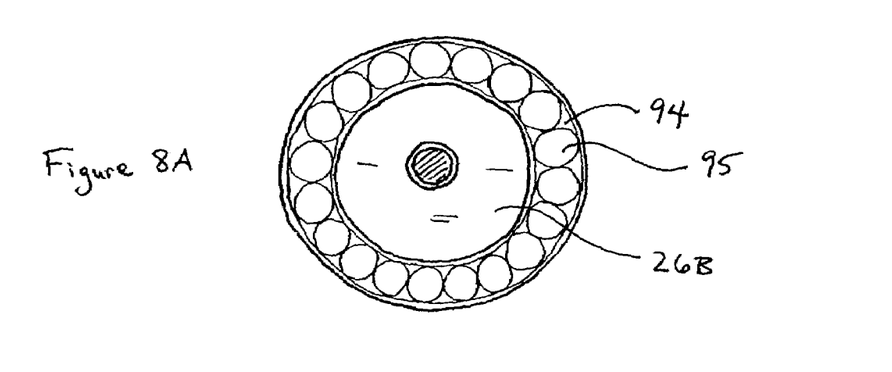
FIG. 8A is top view of an embodiment of a bottom rotation disc.
Figure 8B:
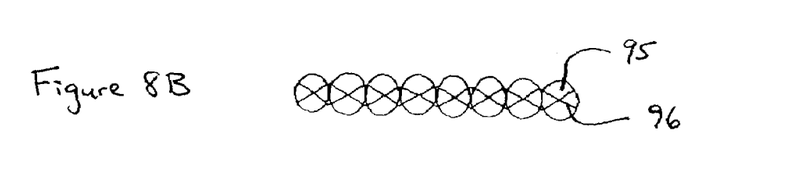
FIG. 8B is side view of ball bearings as arranged in a bottom rotation disc.

FIG. 7 shows an exploded view of a preferred embodiment of the rotation means. A top rotation disc (26A) and a bottom rotation disc (26B) are moveably connected on a rotation shaft (91). A track (94) along the inside of the bottom rotation disc (26B) contains a rotation device, which in this embodiment is ball bearings (95). The ball bearings (95) are shown as small in size in FIG. 7 such that approximately sixty ball bearings (95) fit within the track (94)

around the circumference of the bottom rotation disc (26B). The size of the track and the size of the ball bearings can be varied as shown in FIG. 8. FIG. 8A where nineteen ball bearings (95) are shown to fit within the track (94). As shown in FIG. 8B, an optional brace (96) may be used to allow free rotation of the ball bearings (95) yet holding the ball bearings (95) in position. The brace (96) may be composed of wire, thread or other suitable material. Use of a brace (96) reduces the probability of losing any ball bearings (95) when this embodiment of rotations means is disassembled.

Figure 9:
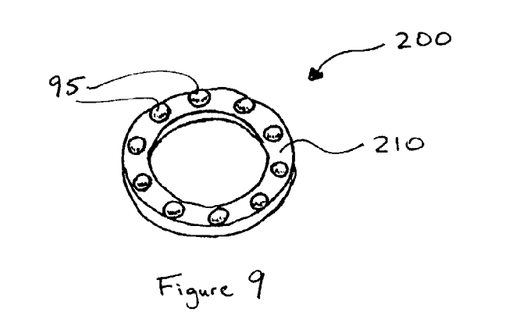
FIG. 9 is perspective view of a ball thrust bearing.
Figure 10A:
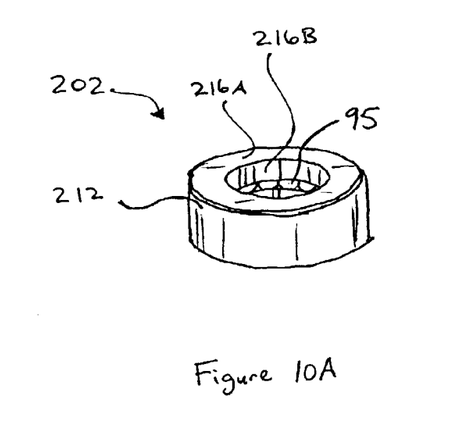
FIG. 10A is a perspective view of an enclosed ball thrust bearing.
Figure 10B:
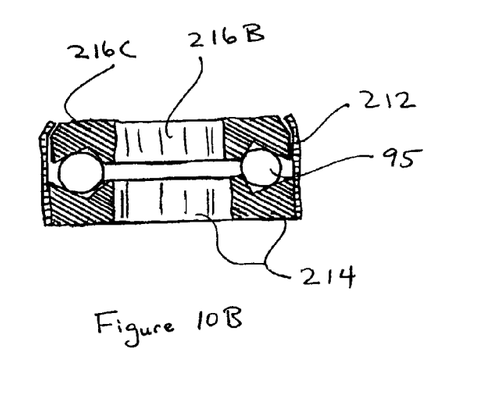
FIG. 10B is a cross section view of an enclosed ball thrust bearing.
Figure 11:
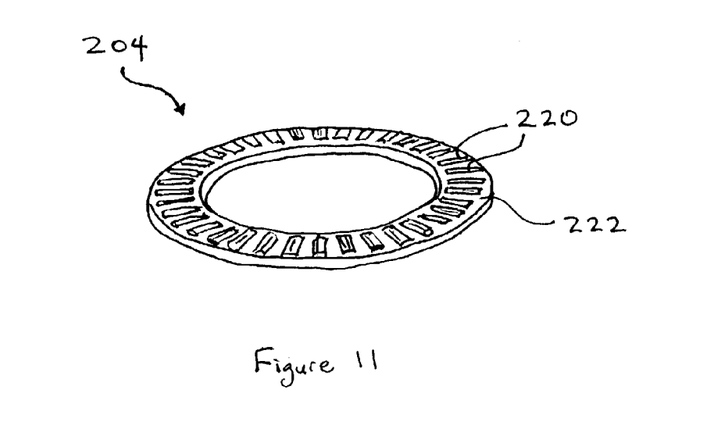
FIG. 11 is a perspective view of a roller thrust bearing.

Examples of alternate rotation devices suitable for placement in the track (94) are shown in FIGS. 9, 10 and 11. FIG. 9 shows a ball thrust bearing (200) where the ball bearings (95) are held in position and spaced apart by spacer apparatus (210).

FIGS. 10A and 10B show a perspective view and a cross sectional view of an enclosed ball thrust bearing (202). The ball bearings (95) are contained between a bottom race (214) and a top race (216). The top race is shown having a top surface (216A) suitable for placement against the inside of the top rotation disc (26A), an inner surface (216B), and a cross section (216C). A sleeve (212) on the outside diameter allows free rotation of the top race (216) relative to a bottom race (214) while preventing separation of the races and exposure of the ball bearings. Utilizing an enclosed ball thrust bearing protects the ball bearings from foreign matter and is advantageous for sterilization.

FIG. 11 shows a perspective view of a roller thrust bearing where roller bearings (220) are held in position and spaced apart by spacer apparatus (222). Each of the ball thrust bearings shown in FIGS. 9 and 10 and the roller thrust bearing shown in FIG. 11 are suitable for placement in the track (94) to facilitate rotation of the top rotation disc (26A) over the bottom rotation disc (26B).

As shown in FIG. 7, a swivel adjustment screw (27) screws onto the rotation shaft (91) to hold the top rotation disc (26A) over the bottom rotation disc (26B). Tightening the swivel adjustment screw (27) over the top rotation disc (26A) creates an immobilizing force such that the top rotation disc cannot rotate about the rotation shaft (91) over the ball bearings (95) and the bottom rotation disc (26B). Conversely, when the swivel adjustment screw (27) is loosened, there is less than a full immobilizing force pushing down on the top rotation disc (26A) is not immobilizing and the top rotation disc (26A) can rotate about the rotation shaft (91). A swivel adjustment stopper (28) can optionally be added to prevent the swivel adjustment screw (27) from being able to completely unscrew from the rotation shaft (91).

Adjustment arm (29) is integrated on the top rotation disc (26A) and has hollow center with a central opening (93) proximal to the curved track (33) on the top rotation disc (26A). Adjustment arm (29) has thread (30) upon which the fine adjustment stopper screw (31) and the fine adjustment screw (32) are attached. The wires (23, 24) are attached to the distal end (51) of the fine adjustment screw (32) as shown in FIG. 4. Unscrewing the fine adjustment screw (32) increases the length of the wires (23, 24) that is held within the adjustment arm (29). This in turn increases the rotational pressure on the left and right blade shaft extensions (15, 16), causing the left and right blades (13, 14) to increase their angular displacement.

The blades (13, 14) are attached to the arms (11, 12) by blade shafts (40) that fit over the utility ends of the arms (11, 12). Blade shafts (40) are attached by a pin (42) and springs (46, 47). Each spring is attached to an arm through a nook, as shown in FIG. 4 for left spring (46) is attached through a nook (50). The springs (46, 47) exert rotational pressure on the arm and the blades to bias the blades into a position where the distal ends (17) of the blades (13, 14) are as close as possible. Use of tension on wires or other rotation means counteracts the spring bias to increase the distance between the distal ends (17) of the blades (13, 14).

Figure 12:
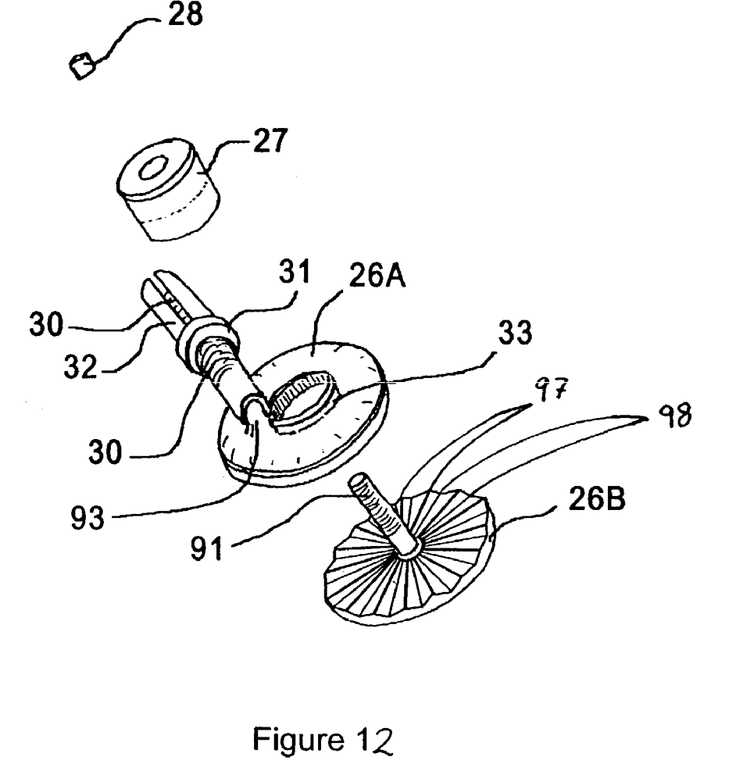
FIG. 12 is an exploded view of an alternate embodiment of rotation means.

FIG. 12 shows an exploded view of an alternate embodiment of the rotation means. As in FIG. 7, a top rotation disc (26A) and a bottom rotation disc (26B) are moveably connected on a rotation shaft (91). In this embodiment, the top and bottom rotation discs (26A, 26B) are movable with respect to each other over a notched or "teeth" system. FIG. 12 shows alternating teeth (97) and grooves (98) on the upper surface of the bottom rotation disc (26B). Corresponding teeth and grooves appear on the lower surface (not shown) of the top rotation disc (26A). When the swivel adjustment screw (27) is loosened, the top rotation disc (26A) can rotate around the rotation shaft (91) over the bottom rotation disc (26B).

Figure 13:
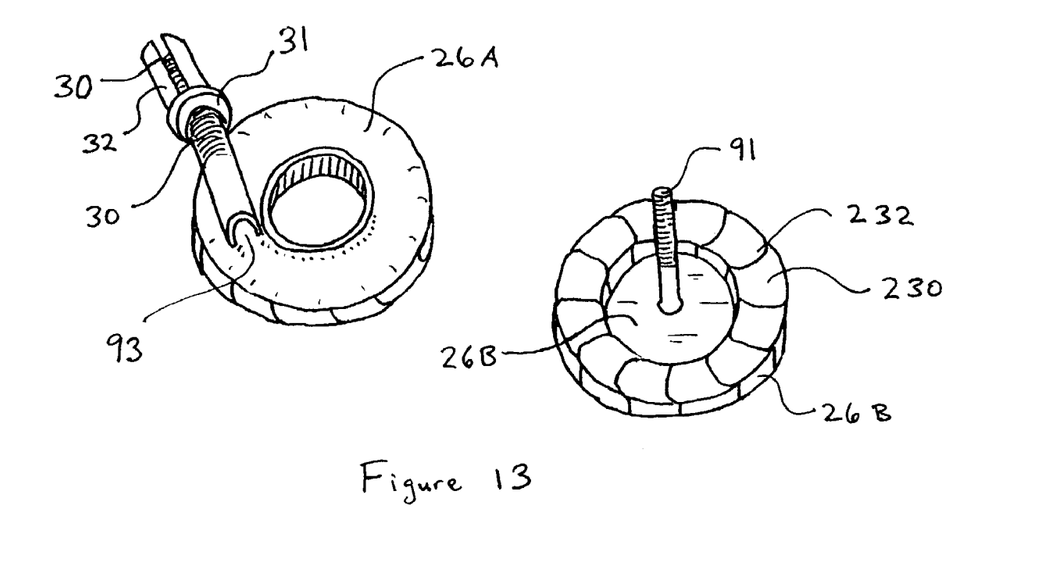
FIG. 13 is a perspective view of a top and bottom rotation disc of an alternate embodiment.

FIG. 13 shows an alternate teeth and groove embodiment. In this embodiment, teeth (230) are arranged along an outside perimeter of the upper surface of the bottom rotation disc (26B). Each tooth (230) has a lip (232) facing in a clockwise direction such that rotation of the top rotation disc (26A) in a clockwise direction is more easily accomplished than rotation in a counter-clockwise direction. The lips (232) are received in corresponding depressions in the lower surface of the top rotation disc (26A).

Figure 14:
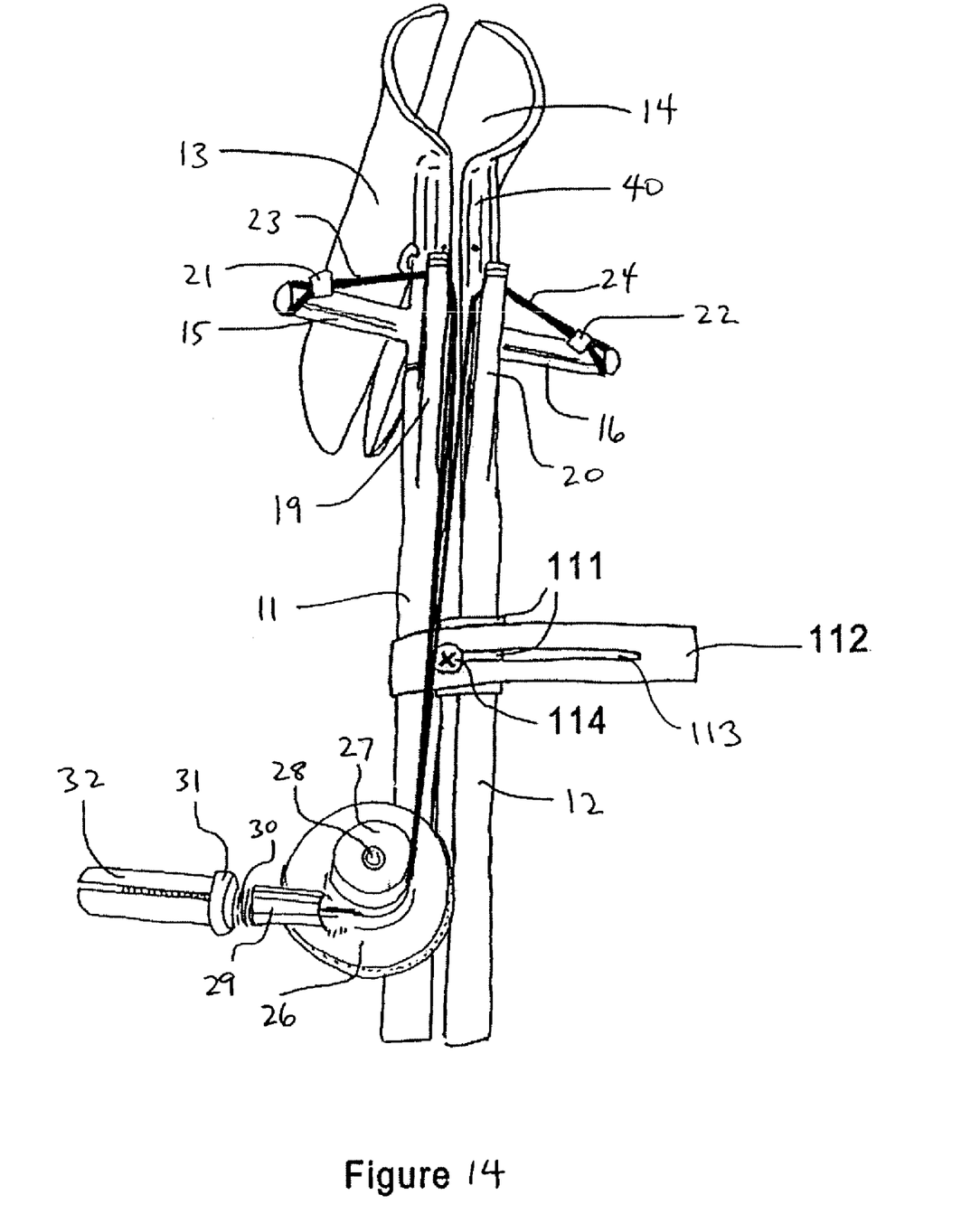
FIG. 14 is a top view of an embodiment having blades in parallel position and in close proximity.

FIG. 14 shows an alternate embodiment of the invention where the handle ends of the left and right arms (11, 12) do not comprise finger holes. The left and right arms (11, 12) are connected by a screw (114) joining first and second attachment devices (111, 112). First attachment device (111) is firmly attached to the right arm (12) and contains an integrally attached nut to accept an attachment screw (114). Second attachment device (112) is firmly attached to the left arm (11) and contains a long slit (113) within which the attachment screw (114) attaches the second attachment device (112) to the first attachment device (111).

Figure 15:
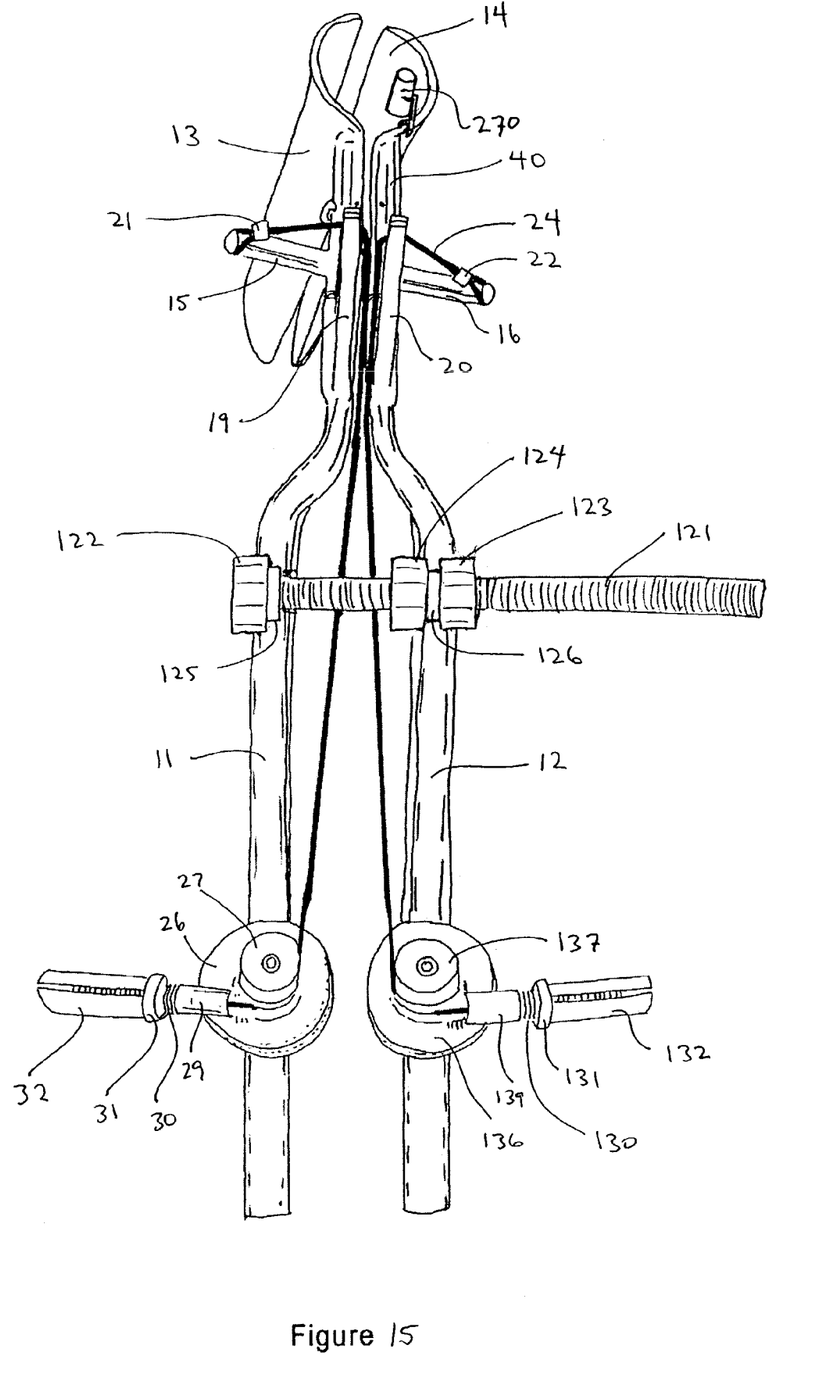
FIG. 15 is a top view of an embodiment having separately pivotally adjustable blades shown in parallel position and in close proximity.

FIG. 15 shows an alternate embodiment of the invention where the left and right arms (11, 12) do not comprise finger holes, and where the left and right blades (13, 14) are separately pivotally adjustable. A second attachment means is shown on the right arm (12) comprising a swivel adjustment stopper (137), a rotation disc (136), an adjustment arm (139) with thread (130), a fine adjustment stopper screw (131) and a fine adjustment screw (132). This second attachment means functions in a similar manner to the embodiment of the attachment means previously described except that in this embodiment each of the first and second attachment means only adjust a single blade. The two arms (11, 12) are attached by nuts (123, 124) and bolt (122). The bolt having a bolt head (122) and screw body (121) is attached to the left arm (11) through a first attachment device (125) and to the right arm (12) through a second attachment device (126). A first nut (124) is adjustable to hold the arms spaced apart. A second nut (123) is adjustable to hold the arms together, preventing the arms (11,12) from sliding apart.

Figure 16:
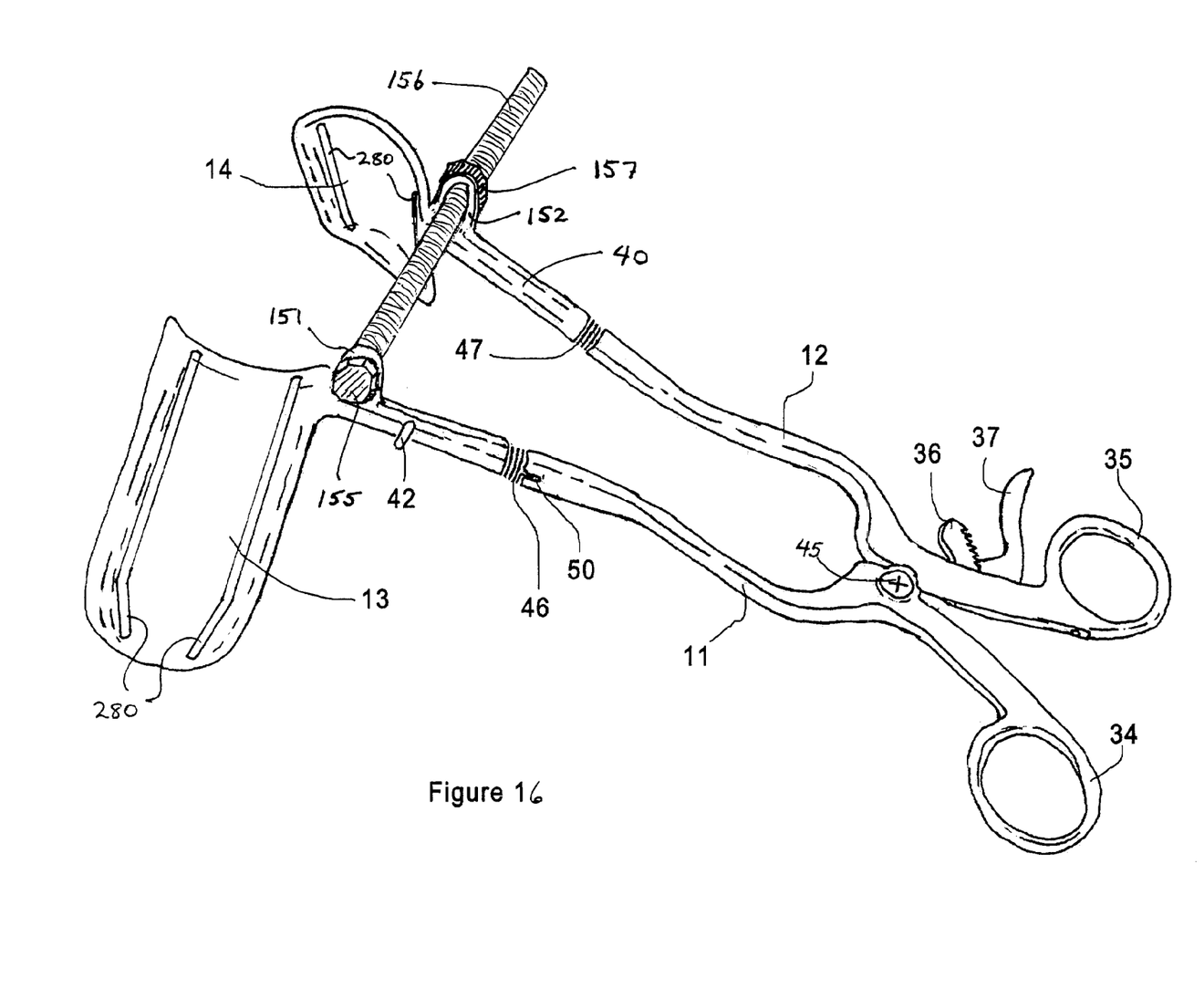
FIG. 16 is a side view of an embodiment having an alternate embodiment of rotation means.

FIG. 16 shows an embodiment with alternate rotation means. The rotation means comprises a first connection extension (151) attached to the left blade (13) and a second connection extension (152) attached to the right blade (14). A rotation bolt having a rotation bolt head (155) and a rotation bolt screw body (156) is attached through the first and second connection extensions (151, 152). A rotation nut (157) screws onto the rotation bolt screw body (156) to adjustably shorten or lengthen the distance between the first and second connection extensions (151, 152). This in turn varies the rotation of the first and second blades (13, 14). The pivot connection (150) between the arms (11, 12) is shown in FIG. 5 and FIG. 16 as a screw (45).

The invention can be practiced with its own light source. A light (270) can be attached to the blades as shown in FIG. 15 or a light source can be contained within a blade such as the fiber optic light source (280) shown in FIG. 16.

Figures 17A, 17C:
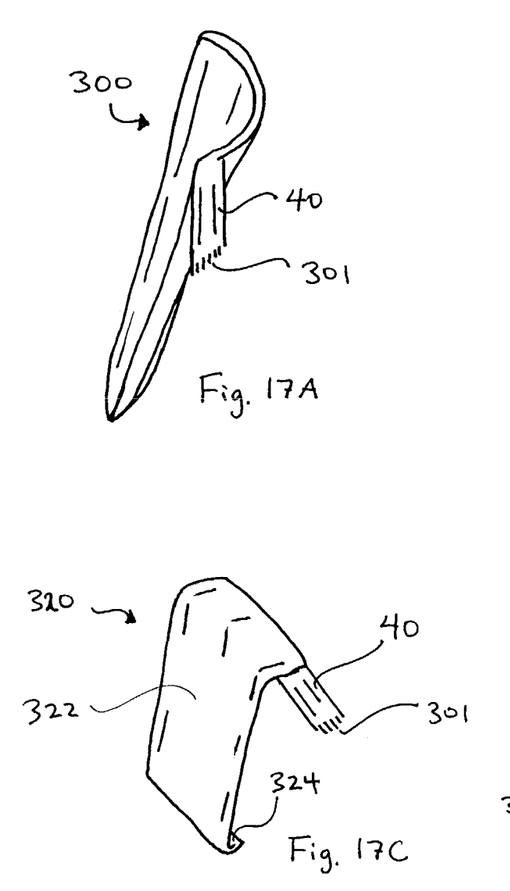
FIGS. 17A, 17B, 17C, 17D, 17E and 17F are perspective views of various blade embodiments.

A solid rounded blade (300) in FIG. 17A has been shown on embodiments throughout the drawings. However, many variations on the shape of the blades are possible such that the invention is suitable for suitable for retracting flesh in a variety of surgical settings without departing from the scope of this invention. Examples of various blade embodiments are shown in FIG. 17. The blade shaft (40) is only partially shown (to point (301)) in FIG. 17 to illustrate only the variations in the blades. Variations on the size and shape of the blades allow the invention to be used to create a well in any operation, increasing access and visualization of deeply located organs or structure through a small opening.

Figure 17B:
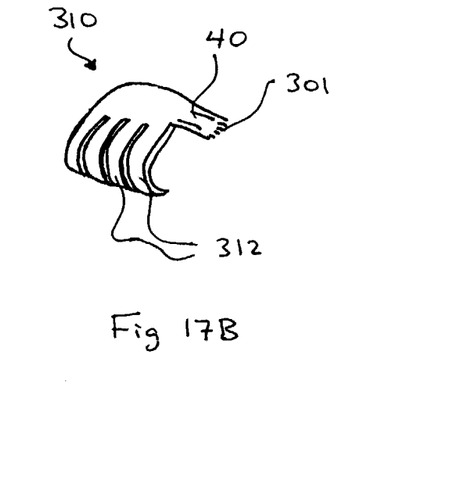
Figure 17D:
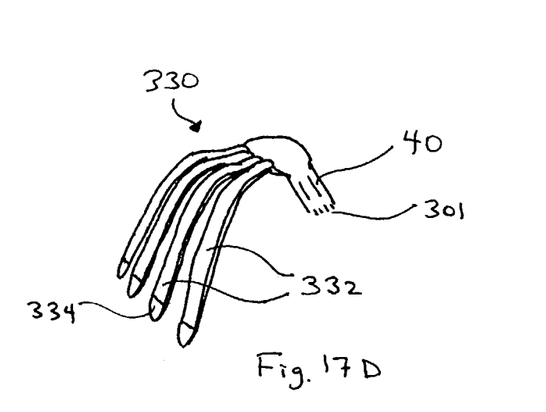
Figure 17E:
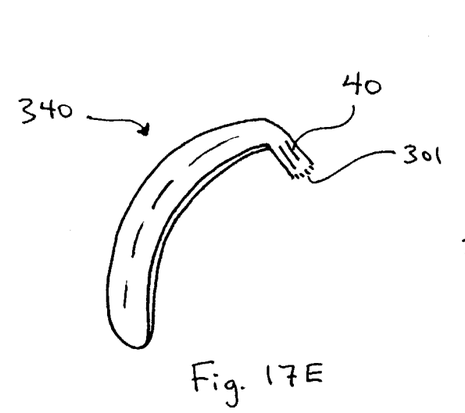
Figure 17F:
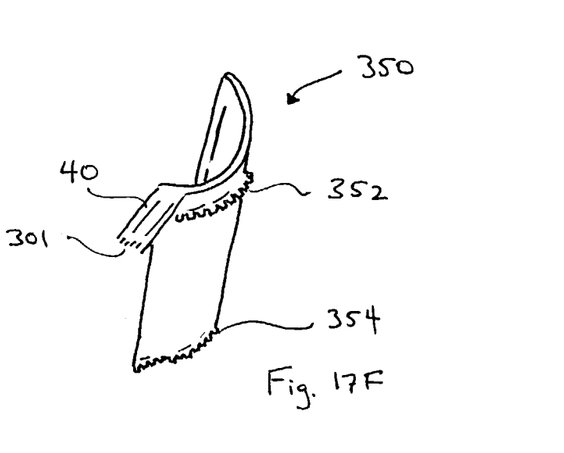

A rake blade (310) is shown in FIG. 17B having rigid fingers (312). A fence blade (320) is shown in FIG. 17C having a substantially flat portion (322) and an outside lip (324). A malleable finger blade (330) is shown in FIG. 17D having fingers (332) and each finger having a tip (334). A solid curved blade (340) is shown in FIG. 17E. A solid rounded blade (350) is shown in FIG. 17F with a row of upper teeth (352) and a row of lower teeth (354). It is to be understood that teeth may be located in any number of positions to maintain stability of the blade and the number of fingers on any blade can be varied. Finally, the invention may be practiced with permanent or with removable or disposable blades. Therefore the blades shown in FIG. 17 are meant to be illustrative but not restrictive.

As will be apparent to those skilled in the art in the light of the foregoing disclosure, many alterations and modifications are possible in the practice of the invention without departing from the spirit or scope thereof. For example at least two embodiments of rotation means have been described, one using wires and a rotation disc and another using a rotation bolt and nut. However the rotation means may encompass any number of different means to adjustably rotate the blades. In addition, the size, shape and dimensions of the instrument can be varied, such as by lengthening the arms, without departing from the scope of the invention. Accordingly, the scope of the invention is to be construed in accordance with the substance defined by the following claims.

What is claimed is:

1. A surgical retractor comprising:
   a first arm having a utility end and a handle end comprising a first finger hole;
   a first blade having proximal and distal ends wherein the proximal end is connected to the utility end of the first arm, the first blade being pivotally and lockably adjustable about the longitudinal axis of the utility end of the first arm;
   a second arm having a finger lever, a ratchet lock, a utility end and a handle end comprising a second finger hole;
   a second blade having proximal and distal ends wherein the proximal end is connected to the utility end of the second arm, the second blade being pivotally and lockably adjustable about the longitudinal axis of the utility end of the second arm;
   a first spring connected to the first blade and the first arm;
   the first spring exerting pressure on the first arm and on the first blade to bias the distal end of the first blade toward the distal end of the second blade;
   a second spring connected to the second blade and the second arm;
   the second spring exerting pressure on the second arm and on the second blade to bias the distal end of the second blade toward the distal end of the first blade;
   wherein the first and second arms are adjustably connected between a closed position having a small distance between the utility end of the first arm and the utility end of the second arm and at least one open position having a larger distance between the utility end of the first arm and the utility end of the second arm and wherein the closed position is further characterized by the utility ends of the first and second arms being substantially parallel; and
   wherein said first and second blades are pivotally and lockably adjustable so as to be capable of providing a larger opening between said blades inside a surgical cavity than at an entrance to said surgical cavity.

2. A surgical retractor as in claim 1, further comprising:
   a first blade shaft connected to the first blade and to the utility end of the first arm;
   a second blade shaft connected to the second blade and to the utility end of the second arm;
   a first blade shaft extension extending outwardly from the first blade shaft;
   a second blade shaft extension extending outwardly from the second blade shaft;
   a first fulcrum connected to the first arm;
   a second fulcrum connected to the second arm;
   a bottom rotation disc connected to the first arm, the bottom rotation disc having a curved track;
   a rotation shaft connected to the first arm extending upwardly from the center of the bottom rotation disc;
   a top rotation disc connected to the bottom rotation disc, the top rotation being pivotally adjustable about the rotation shaft;
   an adjustment arm connected to the top rotation disc, the adjustment arm having a thread;
   a first wire connected to the first blade shaft extension, passing through the first fulcrum, through the curved track of the rotation disc, and through a hollow center of the adjustment arm; and
   a second wire connected to the second blade shaft extension, passing through the second fulcrum, through the curved track of the rotation disc, and through a hollow center of the adjustment arm.

3. A surgical retractor as in claim 1, further comprising:
   a first blade shaft connected to the first blade and to the utility end of the first arm;
   a second blade shaft connected to the second blade and to the utility end of the second arm;
   a first blade shaft extension extending outwardly from the first blade shaft;
   a second blade shaft extension extending outwardly from the second blade shaft;
   a first fulcrum connected to the first arm;
   a second fulcrum connected to the second arm;
   a bottom rotation disc connected to the first arm, the bottom rotation disc having a curved track;
   a rotation shaft connected to the first arm extending upwardly from the center of the bottom rotation disc;
   a top rotation disc connected to the bottom rotation disc, the top rotation being pivotally adjustable about the rotation shaft;

an adjustment arm connected to the top rotation disc;
a first wire connected to the first blade shaft extension, passing through the first fulcrum, through the curved track of the rotation disc, and through a hollow center of the adjustment arm; and
a second wire connected to the second blade shaft extension, passing through the second fulcrum, through the curved track of the rotation disc, and through a hollow center of the adjustment arm.

4. A surgical retractor as in claim 2, further comprising:
a swivel adjustment screw connected to the rotation shaft;
a fine adjustment stopper screw connected to the thread on the adjustment arm;
a fine adjustment screw connected to the thread on the adjustment arm; and
an end of each of the first and second wires connected to a distal end of the fine adjustment screw.

5. A surgical retractor as in claim 4, wherein the wires pass through a fulcrum sleeve connected to the pivot connection of the first and second arms.

6. A surgical retractor as in claim 5, further comprising teeth and grooves on the upper surface of the bottom rotation disc and teeth and grooves on the lower surface of the top rotation disc.

7. A surgical retractor as in claim 5, the bottom rotation disc further comprising a track and a rotation device situated within the track.

8. A surgical retractor as in claim 7, wherein the rotation device is ball bearings.

9. A surgical retractor as in claim 7, wherein the rotation device is a ball thrust bearing.

10. A surgical retractor as in claim 7, wherein the rotation device is an enclosed ball thrust bearing.

11. A surgical retractor as in claim 7, wherein the rotation device is a roller thrust bearing.

12. A surgical retractor as in claim 6, further comprising a swivel adjustment screw stopper attached to a top of the rotation shaft.

13. A surgical retractor as in claim 7, further comprising a swivel adjustment screw stopper attached to a top of the rotation shaft.

14. A surgical retractor as in claim 5, wherein an angle formed between the longitudinal axis of the utility end of the first arm and the longitudinal axis of the left blade is between about 90° and about 120°.

15. A surgical retractor as in claim 1, wherein a light source is coupled to one of the first and second blades.

16. A surgical retractor comprising:
a first arm having a utility end and a handle end comprising a first finger hole;
a first blade connected to the utility end of the first arm, the first blade being pivotally and lockably adjustable about the longitudinal axis of the utility end of the first arm;
a second arm having a finger lever, a ratchet lock, a utility end and a handle end comprising a second finger hole;
said first and second arms being adjustably connected by a pivot connection;
a second blade connected to the utility end of the second arm, the second blade being pivotally and lockably adjustable about the longitudinal axis of the utility end of the second arm;
the first and second arms being adjustably connected between a closed position having a small distance between the utility end of the first arm and the utility end of the second arm and at least one open position having a larger distance between the utility end of the first arm and the utility end of the second arm;
a first spring connected to the first blade and the first arm;
the first spring exerting pressure on the first arm and on the first blade to bias the distal end of the first blade toward the distal end of the second blade;
a second spring connected to the second blade and the second arm;
the second spring exerting pressure on the second arm and on the second blade to bias the distal end of the second blade toward the distal end of the first blade;
the first and second blades each having a proximal end and a distal end, the proximal end of the first blade connected to the utility end of the first arm, the proximal end of the second blade connected to the utility end of the second arm;
wherein the first and second blades are pivotally adjustable in tandem such that as the first blade and second blade are pivotally adjusted, the distal end of the first blade and the distal end of the second blade are substantially equidistant from a plane that is equidistant between the first and second blades when the first and second blades are in substantially parallel position; and
wherein said first and second blades are pivotally and lockably adjustable so as to be capable of providing a larger opening between said blades inside a surgical cavity than at an entrance to said surgical cavity.

17. A surgical retractor as in claim 16, further comprising:
a first blade shaft connected to the first blade and to the utility end of the first arm;
a second blade shaft connected to the second blade and to the utility end of the second arm;
a first blade shaft extension extending outwardly from the first blade shaft;
a second blade shaft extension extending outwardly from the second blade shaft;
a first fulcrum connected to the first arm;
a second fulcrum connected to the second arm;
a bottom rotation disc connected to the first arm, the bottom rotation disc having a curved track;
a rotation shaft connected to the first arm extending upwardly from the center of the bottom rotation disc;
a top rotation disc connected to the bottom rotation disc, the top rotation being pivotally adjustable about the rotation shaft;
an adjustment arm connected to the top rotation disc;
a first wire connected to the first blade shaft extension, passing through the first fulcrum, through the curved track of the rotation disc, and through a hollow center of the adjustment arm; and
a second wire connected to the second blade shaft extension, passing through the second fulcrum, through the curved track of the rotation disc, and through a hollow center of the adjustment arm.

* * * * *